US009949487B1

(12) United States Patent
Hemsarth et al.

(10) Patent No.: US 9,949,487 B1
(45) Date of Patent: Apr. 24, 2018

(54) ECTOPARASITICIDAL FORMULATIONS AND METHODS USING COMBINATIONS OF INSECT GROWTH REGULATORS

(71) Applicant: THE HARTZ MOUNTAIN CORPORATION, Secaucus, NJ (US)

(72) Inventors: W. Lance Hemsarth, Ringwood, NJ (US); Kimberly Cassar, Fair Lawn, NJ (US)

(73) Assignee: THE HARTZ MOUNTAIN CORPORATION, Secaucus, NJ (US)

( * ) Notice: Subject to any disclaimer, the term of this patent is extended or adjusted under 35 U.S.C. 154(b) by 0 days.

(21) Appl. No.: 15/079,845

(22) Filed: Mar. 24, 2016

Related U.S. Application Data

(60) Provisional application No. 62/139,092, filed on Mar. 27, 2015.

(51) Int. Cl.
A01N 49/00 (2006.01)
A01N 43/68 (2006.01)
A01N 31/14 (2006.01)
A01N 31/04 (2006.01)
A01N 43/40 (2006.01)
A01N 43/32 (2006.01)
A01N 31/02 (2006.01)
A01N 43/54 (2006.01)
A01N 51/00 (2006.01)
A01N 43/28 (2006.01)
A01N 53/00 (2006.01)
A01N 43/36 (2006.01)
A01N 47/34 (2006.01)
A01N 37/28 (2006.01)
A01N 43/56 (2006.01)

(52) U.S. Cl.
CPC ............ A01N 49/00 (2013.01); A01N 31/02 (2013.01); A01N 31/04 (2013.01); A01N 31/14 (2013.01); A01N 37/28 (2013.01); A01N 43/28 (2013.01); A01N 43/32 (2013.01); A01N 43/36 (2013.01); A01N 43/40 (2013.01); A01N 43/54 (2013.01); A01N 43/56 (2013.01); A01N 43/68 (2013.01); A01N 47/34 (2013.01); A01N 51/00 (2013.01); A01N 53/00 (2013.01)

(58) Field of Classification Search
CPC ........ A01N 49/00; A01N 31/02; A01N 31/04; A01N 31/14; A01N 37/28; A01N 43/28; A01N 43/32; A01N 43/36; A01N 43/40; A01N 43/54; A01N 43/56; A01N 43/68; A01N 47/34; A01N 51/00; A01N 53/00
See application file for complete search history.

(56) References Cited

U.S. PATENT DOCUMENTS

| 4,166,107 | A | 8/1979 | Miller et al. |
| 4,439,415 | A | 3/1984 | Hennart |
| 5,567,429 | A | 10/1996 | Senbo |
| 5,612,047 | A | 3/1997 | Duffy |
| 5,632,999 | A | 5/1997 | Miller |
| 6,093,415 | A | 7/2000 | Karr |
| 6,096,329 | A | 8/2000 | Jeannin |
| 6,867,223 | B2 | 3/2005 | Cottrell |
| 7,132,448 | B2 | 11/2006 | Cottrell |
| 8,846,722 | B2 | 9/2014 | Ecker |
| 2006/0137241 | A1 | 6/2006 | Yamasaki et al. |
| 2007/0020304 | A1 | 1/2007 | Tamarkin et al. |
| 2008/0118585 | A1* | 5/2008 | Nouvel ................. A01N 65/00 424/739 |
| 2009/0069387 | A1* | 3/2009 | Ecker ..................... A01N 43/40 514/345 |
| 2012/0029025 | A1* | 2/2012 | Nouvel .................. A01N 47/02 514/337 |

FOREIGN PATENT DOCUMENTS

| CA | 2221418 | 11/2008 |
| EP | 0714601 A1 | 6/1996 |
| EP | 0979606 A1 | 2/2000 |
| GB | 2396557 | 6/2004 |
| JP | 04-120002 A | 4/1992 |
| JP | 08-208408 A | 8/1996 |
| JP | 11-060413 A | 3/1999 |
| JP | 2000-109403 A | 4/2000 |
| JP | 2003-026603 A | 1/2003 |
| WO | 1993/0809 | 1/1993 |
| WO | 051116 | 6/2003 |
| WO | 2006/107905 | 10/2006 |
| WO | 041127 | 4/2007 |

(Continued)

OTHER PUBLICATIONS

Bakr et al. (African J Biol Sci. 49-51,55-57; 2005).*
International Search Report and Written Opinion of the International Searching Authority (US) for International Application No. PCT/US2008/075628 dated Dec. 3, 2008.
Office Action dated Mar. 5, 2013 in corresponding Japanese Patent Appln. No. 2010-524227, filed on Sep. 8, 2008, with English Summary of "Notice of Reasons for Rejection."
Extended European Search Report dated Jan. 10, 2013 issued in European Patent Appln. 08829454.1.

(Continued)

Primary Examiner — Umamaheswari Ramachandran
(74) Attorney, Agent, or Firm — Gottlieb, Rackman & Reisman, P.C.

(57) ABSTRACT

A method of and a composition for treating a parasitic infestation in an animal and/or its environment is provided. The method includes providing an ectoparasitcidal formulation which comprises two or more IGRs, in which the IGRs may be selected from the same IGR class or from different IGR classes (excluding two or more juvenile hormone mimic IGRs selected from S-methoprene, hydroprene and pyriproxyfen) and regardless of whether each IGR is mobile or non-mobile or is capable or incapable of translocation in the environment.

8 Claims, No Drawings

(56) References Cited

FOREIGN PATENT DOCUMENTS

WO    WO-2014064681 A1 *  5/2014  ............. A01N 47/34

OTHER PUBLICATIONS

Atkinson, T.H. et al: "Volatile Effects of Insect Growth Regulators Against the German Cockroach *Dictyoptera blattellidae*", Database Accession No. PREV199294038163 *abstract*, Journal of Medical Entomology, vol. 29, No. 2, 1992, pp. 364-367, ISSN: 0022-2585.
Russian Patent Office Official Action for corresponding RU Application No. 2010113006 dated Jul. 9, 2012.
Chinese Patent Office, First Official Action for corresponding CN Application No. 200880105942.9 dated May 25, 2012.
European Patent Office Examination Report for corresponding EP Application No. 08 829 454.4 dated Apr. 11, 2014.
Canadian Patent Office Examination Report for corresponding CA Application No. 2,698,528 dated Sep. 26, 2011.
Chinese Patent Office, Second Official Action for corresponding CN Application No. 200880105942.9 dated Apr. 11, 2013.
Chinese Patent Office, Third Official Action for corresponding CN Application No. 200880105942.9 dated Nov. 15, 2013.
Chinese Patent Office, Fourth Official Action for corresponding CN Application No. 200880105942.9 dated Apr. 16, 2014.

* cited by examiner

ECTOPARASITICIDAL FORMULATIONS AND METHODS USING COMBINATIONS OF INSECT GROWTH REGULATORS

This application claims priority of U.S. provisional patent application No. 62/139,092, filed Mar. 27, 2015.

TECHNICAL FIELD

The present invention relates broadly to compositions and methods for treating animals and/or their environment infested with parasites, and in particular, to topical compositions useful for treating companion animals infested with common ectoparasites. More specifically, this invention relates to improved compositions for treating household pets infested with fleas, ticks and other ectoparasites, to methods of using the same, and to methods for preparing the same.

BACKGROUND OF THE INVENTION

The infestation of companion animals and/or their environment, and in particular household pets such as dogs and cats, with ectoparasitic arthropods such as fleas, ticks and the like, which live by hematophagy (i.e., by sucking the animal's blood), is highly undesirable. The prior art has developed numerous ready-to-use topical formulations and compositions for treating such infestations, many of which are "spot on" or "pour on" formulations that are applied by deposition on the animal's skin.

Such topical applications can be desirable since many formulations are acceptably safe when used topically, even if not when used internally. Topical applications can be more advantageous, however, if the amount of liquid applied to the animal can be minimized. This should be balanced with the need for appropriate dosage to achieve the desired pesticidal effect. Therefore, it is desirable to use highly active insecticides so that the total volume of the insecticide applied to the animal can be minimized.

Topical applications often contain an active component which is an insect growth regulator ("IGR"). IGRs kill immature insects by interfering with the insect's development from the egg and larval stages into adulthood in one or more ways. In general, some IGRs cause the insect to develop too rapidly, while others slow down that development or prevent it from taking place at all. More particularly, IGRs can mimic or disrupt the natural hormones involved in molting and/or exoskeleton formation during arthropod growth while in its immature stages, or they mimic or disrupt the natural juvenile hormones which have an impact on the maturing processes leading to the transition (metamorphosis) of an arthropod from an immature stage to a later immature stage or to the adult stage.

Within these broader categories, IGRs can be further sub-divided into classes, depending upon their mode of action. For example, some IGRs are the natural hormone itself or synthetically created versions thereof, but because they duplicate the effect of the natural hormone, the administration of such IGRs provides an "overdose" which negatively impacts the developmental cycle of the arthropod. Other IGRs act on the natural hormone directly, either interfering with its production or inhibiting its activity, such that the developmental cycle of the arthropod is negatively affected. Still other IGRs can emulate the natural hormones such that they bind to cell surface receptor sites for that hormone, thus acting as agonists or antagonists and preventing the natural hormone from triggering its normal cellular response, thereby also negatively impacting the arthropod's developmental cycle.

It is known that an IGR can have a significant effect on the development of an arthropod, even when used at an extremely low level. It is also known that a combination of two IGRs in the same topical formulation, applied to the same animal so as to be present at the same time, can have an enhanced synergistic effect, rather than the expected, merely additive effect of the two individual IGRs when each is acting alone. However, this synergistic effect was previously thought to be limited to a topical formulation containing two IGRs from the same particular class, specifically, from the class of juvenile hormone mimics. Moreover, this synergistic effect has been found in the situation in which one of the IGRs was a "mobile" (volatile) IGR, that is, an IGR existing as a liquid at room temperature and at atmospheric pressure, and capable of translocation in the environment (examples are methoprene and hydroprene), while the other IGR was a "non-mobile" IGR, that is, an IGR existing in solid form at room temperature and at atmospheric pressure, and which is not capable of translocation within the environment (an example is pyriproxyfen, commercially available under the trademark Nylar™).

It is now believed that a synergistic effect can be achieved with a combination of any two or more IGRs, whether they be from the same class, or from different classes, and regardless of the "mobility" or translocation capability of each. This was not previously anticipated, as many other combinations of pesticide active ingredients from the same or from similar classes of pesticides provide only an additive level of performance, and the synergistic effect mentioned in the preceding paragraph was thought to have resulted solely from the combination of a "mobile" IGR and a "non-mobile" IGR, and only when both are selected from the specific juvenile hormone mimic class of IGRs.

It is therefore the principal object of the present invention to provide ectoparasiticidal formulations for the treatment and protection of companion animals and/or their environment having enhanced efficacy.

It is another object of the present invention to provide ectoparasiticidal compositions that are easy to use.

It is yet a further object of the present invention to provide ectoparasiticidal formulations having a synergistic effect which achieves a higher level of performance than can be achieved using any of the component ingredients individually.

SUMMARY OF THE INVENTION

These and other objects of the present invention are achieved by providing a topical ectoparasitcidal formulation which comprises two or more IGRs, in which the IGRs may be selected from the same IGR class or from different IGR classes (excluding two or more IGRs selected from the class of juvenile hormone mimics), and regardless of whether each IGR is "mobile" or "non-mobile" or is capable or incapable of translocation in the environment.

In one preferred embodiment, the formulation of the invention includes two IGRs and at least one additional insecticide (an "adulticide") which is capable of providing insecticidal activity against adult ectoparasites. The combination of one or more adulticides together with two or more IGRs produces a composition having high ectoparasiticidal activity, thereby providing broad protection against a variety of ectoparasites with a single application of the topical formulation. The use of two or more IGR's has also been determined to lead to a surprising synergistic effect, such as improved activity per total volume ratios. Therefore, the formulation in accordance with the invention provides increased potency, and consequently requires a reduced amount of active ingredients in total.

DETAILED DESCRIPTION OF THE PREFERRED EMBODIMENTS

In accordance with one preferred embodiment of the invention, a method of animal parasite control is provided which involves a combination of two or more IGRs and at least one adulticide that is effective against ectoparasites such as adult fleas and other potential targets. This combination of active ingredients can produce a topical formulation that provides broad protection against ectoparasites.

Preferably, the treatment of different ectoparasites can be targeted by including a particular adulticide including, but not limited to, macrocyclic lactones, natural pyrethrins, synthetic pyrethroids, etofenprox, neo-nicotinoids, phenylpyrazoles, or combinations thereof. The adulticide or combination of adulticides should be present in an amount effective to control ectoparasites in the adult state, preferably between 0.01 and 90 weight percent, and more preferably between 0.1 and 90 weight percent, of the total administration.

At present, the known classes of IGRs include juvenile hormones, juvenile hormone mimics, precocenes, chitin synthesis inhibitors, molting hormones, molting hormone agonists, molting inhibitors, and a class of IGRs whose mode of action has not been confirmed. In accordance with a preferred embodiment of the invention, a topical ectoparasiticidal formulation includes either two or more IGRs selected from one of these classes, or two or more IGRs, selected from at least two different classes; in either case, the selection of two or more IGRs from the class of juvenile hormone mimics is specifically excluded from the invention. The IGRs may be utilized alone or in combination with at least one adulticide.

Juvenile hormones are compounds identified as being produced naturally by arthropods, and which have an impact on metamorphosis. Examples include the substances presently known as Juvenile Hormone I, Juvenile Hormone II, and Juvenile Hormone III.

Juvenile hormone mimics are synthetic compounds that duplicate the effect of natural juvenile hormones. Examples include dayoutong, epofenonane, fenoxycarb, hydroprene, kinoprene, S-methoprene, pyriproxyfen, and triprene.

Precocenes, first derived from plants are compounds that were found to reduce or shut down production of juvenile hormones. Examples include the substances presently known as precocene I, precocene II, and precocene III.

Chitin synthesis inhibitors are compounds which block the formation of chitin, a component of the arthropod exoskeleton. Examples include bistrifluron, chlorbenzuron, chlorfluazuron, dichlorbenzuron, diflubenzuron, flucycloxuron, flufenoxuron, hexaflumuron, lufenuron, novaluron, noviflumuron, penfluron, teflubenzuron, triflumuron, and etoxazole.

Molting hormones are compounds identified as being produced naturally by arthropods, and which have an impact on arthropod molting. Examples include α-ecdysone and ecdysterone.

Molting hormone agonists are synthetic compounds that cause precocious and incomplete molting. Examples include chromafenozide, furan tebufenozide, halofenozide, methoxyfenozide, tebufenozide, and yishijing.

Molting inhibitors are natural or synthetic compounds that block the arthropod molting process. There are at least two types of molting inhibitors: those that act as ecdysone synthesis inhibitors (examples are synthetic azasteroids), and those that act as ecdysteroid receptor antagonists (examples are naturally-occurring cucurbitacins).

In addition, azadirachtin, cyromazine and dicyclanil (the latter two being molting disruptors because they cause molting to happen sooner than normal), are compounds which exhibit IGR activity but for which a mode of action has not yet been confirmed.

The two or more IGRs should be present in an amount effective to control ectoparasites in the juvenile state. The amount of each IGR is preferably between 0.001% and 30.0% by weight, even more preferably between 0.1% and 30.0% by weight, and even more preferably between 0.5% and 20% by weight, of the total administration.

In an embodiment of the invention, the ratio of one IGR to another IGR in the inventive formulation is in the range of 50:1 to 1:50 by weight, preferably in the range of 20:1 to 1:20 range by weight, more preferably in the range of 5:1 and 1:5 by weight, and even more preferably in an approximately 1:1 ratio by weight.

It should be understood that the application of the two or more IGRs, with or without at least one adulticide, can be accomplished without limit to any specific ordering of the application. Thus, it is possible to apply each IGR and the at least one adulticide in a single combined formulation, or separately in succession, and achieve desirable benefits.

In one preferred embodiment of the invention, the insecticide composition of the invention can be packaged in a single dose package. Single dose containers make storage, use, and disposal more convenient for animal owners.

In another preferred embodiment of the invention, the two or more IGRs, with or without the at least one adulticide, can be packaged in a container having two associated, preferably attached, but individual, separated chambers to prevent the mixing of these ingredients prior to the administration to reduce cross-reactivity and improve the shelf-life and efficacy of a formulation where the at least one adulticide needs to be separated from the IGRs. Prior to administration, the packages containing the first and second formulations in their respective separate chambers are opened, and the first and second formulations are dispensed simultaneously or at about the same time to the animal.

In another preferred embodiment of the invention, the IGRs, with or without the at least one adulticide, are applied to the surroundings of the animals' environment, such as a pet bed or a carpet in the home.

In another preferred embodiment of the invention, the IGRs, with or without the at least one adulticide, are prepared in liquid form with a carrier including 1% to 70% aerosol propellants.

In another preferred embodiment of the invention, the IGRs, with or without the at least one adulticide, are prepared in liquid form to be dispensed to surfaces via pump spray.

It is to be understood that the active ingredients need not be mixed together prior to administration of the topical formulation to the animal, but may be stored in suitable carriers separately. Suitable carriers for the IGRs and the at least one adulticide include, but are not limited to, vegetable oils, triglycerides, surfactants, glycols, esters, light petroleum, aldehydes, lactones, triglycerides, amides, silicone polyether copolymers, diakyl fatty acid amides, pyrollidones, aqueous dispersions, alcohols, water, and combinations thereof. The carrier is preferably ethyl lactate. The carriers should be present in an amount between 1% to 99% of the total weight of the composition.

Because compositions in accordance with preferred embodiments of the invention can be formulated with a relatively high concentration of active ingredients, a relatively small application of a spot or line on the animal can effectively prevent and control ectoparasite infestation on the animal for approximately one, two and even four or more weeks post-administration.

In the preparation of a formulation for use on animals, there are several parameters that should be considered. These are: (a) concentration high enough to minimize the volume of the topical applied to the animal (one would not want to put 20 ml, e.g., onto a small dog); (b) concentration low enough to achieve effective translocation of the topical insecticide over the animal's skin; (c) stability for six months at 40 degrees F. and 75% relative humidity, as well as at room temperature and at 20-25 degrees F. (this helps ensure that the formulation remains stable under the conditions that it could meet in commerce); (d) safety when used on the intended animal (particularly non-irritating at least to the intended animal, since the product is applied to the skin), as well as safety if ingested by the animal (ingestion can occur when pets groom themselves); (e) safety to the animal owner; (f) efficacy in use (the composition should kill greater than 90% of the fleas and ticks for up to a minimum of 30 days; (g) avoidance of any reduction of efficacy due to crystallization occurring in the package; (h) aesthetically pleasing (no "oily drop" on the animal when applied); (i) fast drying, so as to reduce the chance of the animal shaking the liquid off, thereby reducing efficacy; and (j) microbiological stability.

It can be advantageous to co-administer additional components to increase the efficacy and to reduce the irritation of insecticides to the skin of animals. The formulation can advantageously contain spreading agents such as n-octyl pyrrolidone, fragrances, and/or antioxidants. Other additives to the insecticidal composition include, but are not limited to, fragrances, surfactants and spreading agents to increase performance, such as polyoxyethylene (20) sorbitan monolaurate (commercially available as polysorbate 20 or Tween® 20) and polyoxyethylene (20) sorbitan monooleate (commercially available as polysorbate 80 or Tween® 80), and isopropyl myristate. Polymers such as agar, gelatin, alginate, and cationic polymers such as cationic guar, cationic cellulose, cationic acrylates, and polyoxymethylene urea may also be added to provide enrobing of the insecticide to improve safety.

In practice, an effective amount of the insecticidal compositions as described herein may be applied to a companion animal, preferably a dog or a cat in a variety of forms, but not limited to a foaming shampoo, dip, aerosol spray, pump spray, powder, lotion, emulsifiable concentrate, aqueous or liquid flowable, slow release collar, suspension concentrate, powder, and by any other methods suitable for administering topical compositions to animals.

In one embodiment of the invention, a method of and a composition for animal parasite control is provided which involves a combination of a juvenile hormone mimic, a molting disrupter and an adulticide. This combination of ingredients can produce a topical formulation which provides broad protection against parasites.

The following examples of formulations containing a juvenile hormone mimic, a molting disrupter and an adulticide are given for illustration purposes only and are not to be construed in a limiting sense.

Example 1

A formulation consistent with an embodiment of the invention is prepared by mixing 2.0% of methoprene, 2.0% of cyromazine, 40.0% of the adulticide etofenprox, 28.0% of ethyl lactate and 28.0% of diethylene glycol monoethyl ether.

Example 2

A formulation consistent with an embodiment of the invention is prepared by mixing 3.0% of methoprene, 3.0% of dicyclanil, 10.0% of the adulticide dinotefuran, 42.0% of benzyl alcohol and 42% of propylene carbonate.

Example 3

A formulation consistent with an embodiment of the invention is prepared by mixing 2.0% of pyriproxyfen, 2.0% of cyromazine, 10.0% of the adulticide imidacloprid, 43.0% of propylene carbonate and 43.0% of phenoxyethanol.

Example 4

A formulation consistent with an embodiment of the invention is prepared by mixing 2.0% of pyriproxyfen, 2.0% of dycyclanil, 40.0% of pyrethrins, 28.0% of n-octyl pyrrolidone and 28.0% of propylene carbonate.

In another embodiment of the invention, a method of and a composition for animal parasite control is provided which involves a combination of a juvenile hormone mimic, a precocene and an adulticide. This combination of ingredients can produce a topical formulation which provides broad protection against parasites.

The following examples of formulations containing a juvenile hormone mimic, a precocene and an adulticide are given for illustration purposes only and are not to be construed in a limiting sense.

Example 5

A formulation consistent with an embodiment of the invention is prepared by mixing 3.0% of methoprene, 3.0% of precocene I, 40% of the adulticide permethrin, 27.0% of N-methyl pyrrolidone and 27.0% of n-octyl pyrrolidone.

Example 6

A formulation consistent with an embodiment of the invention is prepared by mixing 2.0% of pyriproxyfen, 2.0% of precocene I, 40.0% of pyrethrins, 28.0% of n-octyl pyrrolidone and 28.0% of isopropyl myristate.

Yet in another embodiment of the invention, a method of and a composition for animal parasite control is provided which involves a combination of a juvenile hormone mimic, a chitin synthesis inhibitor and an adulticide. This combination of ingredients can produce a topical formulation which provides broad protection against parasites.

The following examples of formulations containing a juvenile hormone mimic, a chitin synthesis inhibitor and an adulticide are given for illustration purposes only and are not to be construed in a limiting sense.

Example 7

A formulation consistent with an embodiment of the invention is prepared by mixing 2.0% of methoprene, 2.0% of chlorfluazuron, 40.0% of the adulticide etofenprox, 40.0% of N-methyl pyrrolidone and 16.0% of diethylene glycol monoethyl ether.

Example 8

A formulation consistent with an embodiment of the invention is prepared by mixing 1.0% of pyriproxyfen, 1.0% of chlorfluazuron, 10.0% of the adulticide imidacloprid, 44.0% of benzyl alcohol and 44.0% of propylene carbonate.

Still in another embodiment of the invention, a method of and composition for animal parasite control is provided which involves a combination of a juvenile hormone mimic, a molting hormone agonist and an adulticide. This combination of ingredients can produce a topical formulation which provides broad protection against parasites.

The following examples of formulations containing a juvenile hormone mimic, a molting hormone agonist and an adulticide are given for illustration purposes only and are not to be construed in a limiting sense.

Example 9

A formulation consistent with an embodiment of the invention is prepared by mixing 2.0% of methoprene, 2.0% of methoxyfenozide, 40% of pyrethrins, 28.0% of n-octyl pyrrolidone and 28.0% of diethylene glycol monoethyl ether.

Example 10

A formulation consistent with an embodiment of the invention is prepared by mixing 1.0% of pyriproxyfen, 1.0% of methoxyfenozide, 40.0% of the adulticide permethrin, 29.0% of n-methyl pyrrolidone and 29.0% of diethylene glycol monoethyl ether.

In another embodiment of the invention, a method of and composition for animal parasite control is provided which involves a combination of two molting disrupter, a precocene and an adulticide. This combination of ingredients can produce a topical formulation which provides broad protection against parasites.

The following example of a formulation containing a molting disrupter, a precocene and an adulticide is given for illustration purposes only and are not to be construed in a limiting sense.

Example 11

A formulation consistent with an embodiment of the invention is prepared by mixing 3.0% of dicylanil, 3.0% of precocene I, 10.0% of the adulticide dinotefuran, 42.0% of ethyl lactate and 42.0% of isopropyl myristate.

In another embodiment of the invention, a method of and composition for animal parasite control is provided which involves a combination of a molting disrupter, a chitin synthesis inhibitor and an adulticide. This combination of ingredients can produce a topical formulation which provides broad protection against parasites.

The following example of a formulation containing a molting disrupter, a chitin synthesis inhibitor and an adulticide is given for illustration purposes only and is not to be construed in a limiting sense.

Example 12

A formulation consistent with an embodiment of the invention is prepared by mixing 3.0% of dicylanil, 3.0% of chlorfluazuron, 10.0% of the adulticide imidacloprid, 42.0% of n-methyl pyrrolidone and 42.0 of benzyl alcohol.

In one embodiment of the invention, a method of and composition for animal parasite control is provided which involves a combination of a molting disrupter, a molting hormone agonist and an adulticide. This combination of ingredients can produce a topical formulation which provides broad protection against parasites.

The following example of a formulation containing a molting-disrupter, a molting hormone agonist and an adulticide is given for illustration purposes only and is not to be construed in a limiting sense.

Example 13

A formulation consistent with an embodiment of the invention is prepared by mixing 4.0% of dicyclanil, 4.0% of methoxyfenozide, 10.0% of the adulticide fipronil, 10.0% of ethanol and 72.0% of n-methyl pyrrolidone.

In another embodiment of the invention, a method of and composition for animal parasite control is provided which involves a combination of two different molting disrupters and an adulticide. This combination of ingredients can produce a topical formulation which provides broad protection against parasites.

The following example of a formulation containing two different molting disrupters and an adulticide is given for illustration purposes only and is not to be construed in a limiting sense.

Example 14

A formulation consistent with an embodiment of the invention is prepared by mixing 2.0% of dicyclanil, 2.0% of cyromazine, 30.0% of pyrethrins, 33.0% of n-octyl pyrrolidone and 33.0% of diethylene glycol monoethyl ether.

In one embodiment of the invention, a method of and composition for animal parasite control is provided which involves a combination of a chitin synthesis inhibitor, a molting hormone agonist and an adulticide. This combination of ingredients can produce a topical formulation which provides broad protection against parasites.

The following example of a formulation containing a chitin synthesis inhibitor, a molting hormone agonist, and an adulticide is given for illustration purposes only and is not to be construed in a limiting sense.

Example 15

A formulation consistent with an embodiment of the invention is prepared by mixing 1.0% of chlorfluazuron, 1.0% of methoxyfenozide, 40.0% of the adulticide permethrin, 29.0% of n-methyl pyrrolidone and 29.0% of ethyl lactate.

In another embodiment of the invention, a method of and composition for animal parasite control is provided which involves a combination of a chitin synthesis inhibitor, a precocene and an adulticide. This combination of ingredients can produce a topical formulation which provides broad protection against parasites.

The following example of a formulation containing a chitin synthesis inhibitor, a precocene, and an adulticide is given for illustration purposes only and is not to be construed in a limiting sense.

Example 16

A formulation consistent with an embodiment of the invention is prepared by mixing 3.0% of chlorfluazuron, 3.0% of precocene I, 40.0% of the adulticide etofenprox, 27.0% of diethylene glycol monoethyl ether and 27.0% of ethyl lactate.

In another embodiment of the invention, a method of animal parasite control is provided which involves a combination of a juvenile hormone mimic and a molting disrupter, with or without an adulticide. This combination of ingredients can produce a spray formulation which provides a broad environmental parasite infestation control barrier.

The following example of a formulation containing a juvenile hormone mimic and a molting disruptor, with or without an adulticide, is given for illustration purposes only and is not to be construed in a limiting sense.

Example 17

A formulation consistent with an embodiment of the invention for treatment of the pet's environment is prepared by mixing 0.1% of pyriproxyfen, 0.1% dicyclanil, 4.0% Tween®20, 2.0% N-methyl pyrrolidone and 93.8% water.

In another embodiment of the invention, a method of animal parasite control is provided which involves a combination of a juvenile hormone mimic, a chitin synthesis inhibitor, with or without and an adulticide. This combination of ingredients can produce a powder formulation which provides a broad environmental parasite infestation control barrier.

The following example of a formulation containing a juvenile hormone mimic and a chitin synthesis inhibitor, with or without an adulticide, is given for illustration purposes only and is not to be construed in a limiting sense.

Example 18

A powder formulation consistent with an embodiment of the invention is prepared by mixing 2.0% of methoprene, 2.0% of chlorfluazuron, 40.0% of precipitated calcium carbonate and 56.0% corn starch.

While there has been described what are at present considered to be the preferred embodiments of the present invention, it will be apparent to those skilled in the art that the embodiments described herein are by way of illustration and not of limitation. Various modifications of the disclosed embodiments, as well as alternative embodiments of the invention, will become apparent to persons skilled in the art upon reference to the description of the invention. Therefore, it is to be understood that various changes and modifications may be made in the embodiments disclosed herein without departing from the true spirit and scope of the present invention, as set forth in the appended claims, and it is contemplated that the appended claims will cover any such modifications or embodiments.

The invention claimed is:

1. A method of treating a parasitic infestation in a non-human animal, the method comprising topically co-administering to the animal two different insect growth regulators comprising the juvenile hormone mimic methoprene and the chitin synthesis inhibitor chlorfluazuron, wherein said parasitic infestation comprises an infestation of hematophagic ectoparasitic arthropods and wherein the ratio of one insect growth regulator to another insect growth regulator is 5:1 to 1:5.

2. The method of claim 1, wherein each insect growth regulator is present in an amount between 0.001% and 30.0% by weight of the total administration.

3. The method of claim 1, wherein said co-administration step further comprises co-administering to said animal at least one adulticide effective to kill adult fleas and ticks.

4. The method of claim 1, wherein each insect growth regulator component is present in an amount between 0.5% and 20.0% by weight of the total administration.

5. The method of claim 3, wherein the at least one adulticide is at least one pyrethroid.

6. The method of claim 5, wherein the at least one pyrethroid is etofenprox.

7. The method of claim 3, wherein the at least one adulticide is present in an amount between about 0.1% and 90.0%.

8. The method of claim 1, wherein the co-administration step comprises applying said juvenile hormone mimic and said chitin synthesis inhibitor onto said animal substantially simultaneously.

\* \* \* \* \*